US012616413B2

(12) United States Patent
Engebretsen et al.

(10) Patent No.: US 12,616,413 B2
(45) Date of Patent: *May 5, 2026

(54) BEAT AND RHYTHM RECLASSIFICATION

(71) Applicant: Preventice Solutions, Inc., Rochester, MN (US)

(72) Inventors: David Engebretsen, Cannon Falls, MN (US); Benjamin Adam Teplitzky, Lakeville, MN (US); Jake Matras, Eagan, MN (US); Michael Thomas Edward McRoberts, Mazeppa, MN (US); Timothy McClanahan, Rochester, MN (US)

(73) Assignee: Preventice Solutions, Inc., Rochester, MN (US)

( * ) Notice: Subject to any disclaimer, the term of this patent is extended or adjusted under 35 U.S.C. 154(b) by 399 days.

This patent is subject to a terminal disclaimer.

(21) Appl. No.: 18/140,350

(22) Filed: Apr. 27, 2023

(65) Prior Publication Data

US 2023/0414155 A1 Dec. 28, 2023

Related U.S. Application Data

(60) Provisional application No. 63/336,071, filed on Apr. 28, 2022.

(51) Int. Cl.
*A61B 5/361* (2021.01)
*A61B 5/00* (2006.01)
(Continued)

(52) U.S. Cl.
CPC ............ *A61B 5/361* (2021.01); *A61B 5/0006* (2013.01); *A61B 5/0022* (2013.01); *A61B 5/363* (2021.01); *G16H 40/67* (2018.01); *A61B 5/7475* (2013.01)

(58) Field of Classification Search
CPC . A61B 5/0006; A61B 5/0022; A61B 5/02438; A61B 5/349; A61B 5/361;
(Continued)

(56) References Cited

U.S. PATENT DOCUMENTS

| | | | |
|---|---|---|---|
| 2008/0140143 A1* | 6/2008 | Ettori ...................... | A61B 5/35 |
| | | | 607/14 |
| 2014/0163634 A1* | 6/2014 | Ghosh ................ | A61N 1/37247 |
| | | | 607/28 |

(Continued)

*Primary Examiner* — George Manuel
(74) *Attorney, Agent, or Firm* — Faegre Drinker Biddle & Reath, LLP

(57) ABSTRACT

A method includes receiving—by a first computing system—electrocardiogram (ECG) data and metadata associated with the ECG data, where the metadata includes an initial cardiac event classification and an initial beat classification for beats occurring during a first event associated with the initial cardiac event classification. The method further includes causing the ECG data to be displayed in a user interface (UI) and receiving a command, via the UI, to change the initial beat classifications to subsequent beat classifications. The method also includes automatically modifying, by the first computing system, the initial cardiac event classification to a subsequent cardiac event classification based on the subsequent beat classifications.

20 Claims, 11 Drawing Sheets

(51) Int. Cl.
A61B 5/363 (2021.01)
G16H 40/67 (2018.01)

(58) Field of Classification Search
CPC ..... A61B 5/363; A61B 5/7267; A61B 5/7282;
A61B 5/742; A61B 5/7475; G06N
3/0455; G06N 3/0464; G06N 3/048;
G06N 3/088; G16H 40/67; G16H 50/20
See application file for complete search history.

(56) References Cited

U.S. PATENT DOCUMENTS

2021/0007618 A1* 1/2021 Cao ........................ A61B 5/355
2021/0338135 A1* 11/2021 Xia .......................... A61B 5/36

* cited by examiner

BEAT AND RHYTHM RECLASSIFICATION

CROSS REFERENCE TO RELATED APPLICATION

This application claims priority to Provisional Application No. 63/336,071, filed Apr. 28, 2022, all of which are herein incorporated by reference in their entirety.

TECHNICAL FIELD

The present disclosure relates to devices, methods, and systems for analyzing cardiac activity and cardiac events.

BACKGROUND

Monitoring devices for collecting biometric data are becoming increasingly common in diagnosing and treating medical conditions in patients. For example, mobile devices can be used to monitor cardiac data in a patient. This cardiac monitoring can empower physicians with valuable information regarding the occurrence and regularity of a variety of heart conditions and irregularities in patients. Cardiac monitoring can be used, for example, to identify abnormal cardiac rhythms, so that critical alerts can be provided to patients, physicians, or other care providers and patients can be treated.

SUMMARY

In Example 1, a method includes receiving—by a first computing system—electrocardiogram (ECG) data and metadata associated with the ECG data, where the metadata includes an initial cardiac event classification and an initial beat classification for beats occurring during a first event associated with the initial cardiac event classification. The method further includes causing the ECG data to be displayed in a user interface (UI) and receiving a command, via the UI, to change the initial beat classifications to subsequent beat classifications. The method also includes automatically modifying, by the first computing system, the initial cardiac event classification to a subsequent cardiac event classification based on the subsequent beat classifications.

In Example 2, the method of Example 1, wherein the automatically modifying the initial cardiac event classification to the subsequent cardiac event classification includes using a state machine.

In Example 3, the method of Example 2, wherein the state machine uses the subsequent beat classifications to determine the subsequent cardiac event classification.

In Example 4, the method of any of Examples 2 or 3, wherein the state machine uses the initial beat classifications of beats surrounding the first event to determine the subsequent cardiac event classification.

In Example 5, the method of any of Examples 2-4, wherein a multi-step algorithm receives outputs of the state machine, wherein the multi-step algorithm determines the subsequent cardiac event classification.

In Example 6, the method of any of the preceding Examples, wherein the command causes the initial beat classifications to change to the subsequent beat classifications for thousands of individual beats.

In Example 7, the method of any of the preceding Examples, wherein the metadata comprises initial cardiac event classifications and initial beat classification for beats occurring during multiple events, wherein only the initial cardiac event classifications associated with subsequent beat classifications are modified.

In Example 8, the method of any of the preceding Examples, wherein the automatically modifying the initial cardiac event classification to the subsequent cardiac event classification causes initial separate events to merge into a single event.

In Example 9, the method of any of the preceding Examples, further including: displaying, via the UI in a single window, multiple superimposed plots of beats associated with the same initial beat classification.

In Example 10, the method of Example 9, wherein the command includes selecting some or all of the beats in the single window and modifying the initial beat classifications to the subsequent beat classifications.

In Example 11, the method of any of the preceding Examples, wherein the initial beat classifications are ventricular beats and the subsequent beat classifications are normal beats, wherein the initial cardiac event classification is a sinus rhythm and the subsequent event classification is an atrial fibrillation rhythm.

In Example 12, the method of any of the preceding Examples, wherein wherein the initial beat classifications are ventricular beats and the subsequent beat classifications are supraventricular beats, wherein the subsequent event classification is a supraventricular tachycardia event.

In Example 13, a computer program product comprising instructions to cause one or more processors to carry out the steps of the method of Example 12.

In Example 14, a computer-readable medium having stored thereon the computer program product of Example 13.

In Example 15, a computer comprising the computer-readable medium of Example 14.

In Example 16, a system includes a remote computing system with: a user interface (UI), a first processor, and a first computer-readable medium having a first set of computer-executable instructions embodied thereon. The first set of instructions are configured to be executed by the first processor to cause the first processor to: display the ECG data in the UI after receiving electrocardiogram (ECG) data and metadata including an initial cardiac event classification and an initial beat classification for beats occurring during a first event associated with the initial cardiac event classification; receive a command to change the initial beat classifications to subsequent beat classifications; and automatically modify the initial cardiac event classification to a subsequent cardiac event classification based on the subsequent beat classifications.

In Example 17, the system of Example 16, wherein the command is generated in response to receiving input, via the UI, from a user.

In Example 18, the system of Example 16, wherein the automatically modifying the initial cardiac event classification to the subsequent cardiac event classification includes using a state machine.

In Example 19, the system of Example 18, wherein the state machine uses the subsequent beat classifications to determine the subsequent cardiac event classification.

In Example 20, the system of Example 18, wherein the state machine uses the initial beat classifications of beats surrounding the first event to determine the subsequent cardiac event classification.

In Example 21, the system of Example 18, wherein a multi-step algorithm receives outputs of the state machine, wherein the multi-step algorithm determines the subsequent cardiac event classification.

In Example 22, the system of Example 16, wherein the command causes the initial beat classifications to change to the subsequent beat classifications for thousands of individual beats.

In Example 23, the system of Example 16, wherein the metadata comprises initial cardiac event classifications and initial beat classification for beats occurring during multiple events, wherein only the initial cardiac event classifications associated with subsequent beat classifications are modified.

In Example 24, the system of Example 16, wherein the automatically modifying the initial cardiac event classification to the subsequent cardiac event classification causes initial separate events to merge into a single event.

In Example 25, the system of Example 16, wherein the first set of instructions further cause the first processor to: display, via the UI in a single window, multiple superimposed plots of beats associated with the same initial beat classification.

In Example 26, the system of Example 25, wherein the command comprises selecting some or all of the beats in the single window and modifying the initial beat classifications to the subsequent beat classifications.

In Example 27, the system of Example 16, wherein the initial beat classifications are ventricular beats and the subsequent beat classifications are normal beats, wherein the initial cardiac event classification is a sinus rhythm and the subsequent event classification is an atrial fibrillation rhythm.

In Example 28, the system of Example 16, wherein the initial beat classifications are ventricular beats and the subsequent beat classifications are supraventricular beats, wherein the subsequent event classification is a supraventricular tachycardia event.

In Example 29, the system of Example 16, wherein the first set of instructions are configured to be executed via a web browser at the remote computing system.

In Example 30, the system of Example 16, further including a server with: a database, a second processor, and a second computer-readable medium having a second set of computer-executable instructions embodied thereon. The second set of instructions configured to be executed by the second processor to cause the second processor to: determine, using a machine learning model operated by the server and based on ECG data, the initial cardiac event classification and the initial beat classifications; store the initial cardiac event classification and initial beat classifications in the database; transmit, to the remote computing system, strips of the initial ECG data, the initial cardiac event classification, the initial beat classifications, and the first set of instructions; receive, from the remote computing system, the subsequent cardiac event classification and the subsequent beat classifications; and replace, in the database, the initial cardiac event classification with the subsequent cardiac event classification and the initial beat classifications with the subsequent beat classifications.

While multiple instances are disclosed, still other instances of the present disclosure will become apparent to those skilled in the art from the following detailed description, which shows and describes illustrative instances of the disclosure. Accordingly, the drawings and detailed description are to be regarded as illustrative in nature and not restrictive.

Figure 1:
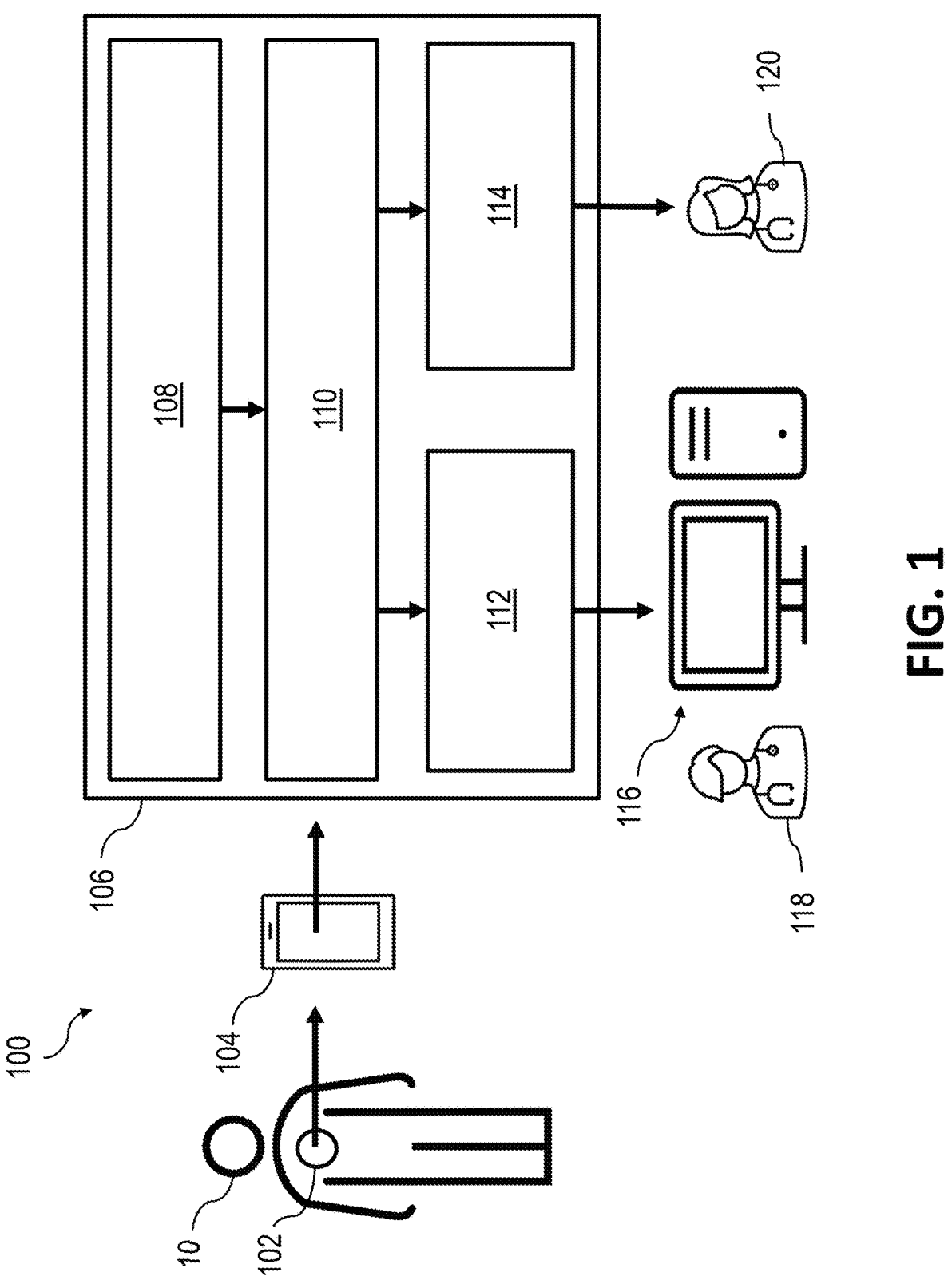
FIG. 1 shows a cardiac monitoring system, in accordance with certain instances of the present disclosure.

While the disclosed subject matter is amenable to various modifications and alternative forms, specific instances have been shown by way of example in the drawings and are described in detail below. The intention, however, is not to limit the disclosure to the particular instances described. On the contrary, the disclosure is intended to cover all modifications, equivalents, and alternatives falling within the scope of the disclosure as defined by the appended claims.

DETAILED DESCRIPTION

The present disclosure relates to devices, methods, and systems for facilitating analysis of cardiac activity and cardiac events (e.g., abnormal cardiac rhythms or other issues).

Electrocardiogram (ECG) data of a patient can be used to identify whether the patient has experienced a cardiac event and what type of cardiac event occurred. One input to determining the type of cardiac event includes the types (or classifications) of heartbeats experienced during the cardiac event. As such, an ECG analysis system may automatically determine that a certain type of cardiac event occurred based on—among other things—how the system classified the beats occurring during the event. However, if the beats were initially misclassified, the determined type of cardiac event may also be misclassified and therefore may then need to be reclassified. Instances of the present disclosure are accordingly directed to systems, methods, and devices for facilitating reclassification of ECG data.

FIG. 1 illustrates a patient 10 and an example system 100. The system 100 includes a monitor 102 attached to the patient 10 to detect cardiac activity of the patient 10. The monitor 102 may produce electric signals that represent the cardiac activity in the patient 10. For example, the monitor 102 may detect the patient's heart beating (e.g., using infrared sensors, electrodes) and convert the detected heartbeat into electric signals representing ECG data. The monitor 102 communicates the ECG data to a mobile device 104 (e.g., a mobile phone).

The mobile device 104 may include a program (e.g., mobile phone application) that receives, processes, and analyzes the ECG data. For example, the program may analyze the ECG data and detect or flag cardiac events (e.g., periods of irregular cardiac activity) contained within the ECG data. As noted above, because ECG data may be getting continuously generated, the amount of ECG data can be overwhelming to store and process locally on the mobile device 104. As such, the mobile device 104 can periodically transmit chunks of the ECG data to another device or system, which can process, append together, and archive the chunks of the ECG data and metadata (e.g., time, duration, detected/flagged cardiac events) associated with the chunks of ECG data. In certain instances, the monitor 102 may be programmed to transmit the ECG data directly to the other device or system without utilizing the mobile device 104. Also, in certain instances, the monitor 102 and/or the mobile device 104 includes a button or touch-screen icon that allows the patient 10 to initiate an event. Such an indication can be recorded and communicated to the other device or system. In other instances involving multi-day studies, the ECG data and associated metadata are transmitted in larger chunks.

Cardiac Event Server

In the example shown in FIG. 1, the mobile device 104 transmits the ECG data (and associated metadata, if any) to a cardiac event server 106 (hereinafter "the server 106" for brevity). The server 106 includes multiple platforms, layers, or modules that work together to process and analyze the ECG data such that cardiac events can be detected, filtered, prioritized, and ultimately reported to a patient's physician for analysis and treatment. In the example of FIG. 1, the server 106 includes one or more machine learning models 108 (e.g., deep neural networks), a cardiac event router 110, a report platform 112, and a notification platform 114. Although only one server 106 is shown in FIG. 1, the server 106 can include multiple separate physical servers, and the various platforms/modules/layers can be distributed among the multiple servers. Each of the platforms/modules/layers can represent separate programs, applications, and/or blocks of code where the output of one of the platforms/modules/layers is an input to another of the platforms/modules/layers. Each platform/module/layer can use application programming interfaces to communicate between or among the other platforms/modules/layers as well as systems and devices external to the server 106.

Machine Learning Model

The server 106 applies the machine learning model 108 to the ECG data to classify cardiac activity of the patient 10. As described in more detail below, at a high level, the machine learning model 108 is programmed to—among other things—compare the ECG data to labeled ECG data to determine which labeled ECG data the ECG data most closely resembles. The labeled ECG data may identify a particular cardiac event—including but not limited to ventricular tachycardia, bradycardia, atrial fibrillation, pause, normal sinus rhythm, or artifact/noise—as well as particular beat types—including but not limited to ventricular, normal, or supraventricular.

In certain embodiments, the machine learning model 108 includes three paths or separate neural networks (e.g., deep neural networks). These neural networks can be used in parallel, although certain outputs from the neural networks can be inputted to another one of the neural networks.

The first neural network of the machine learning model 108 is an unsupervised trained neural network that recognizes and groups beats with a similar shapes (e.g., similar waveforms). The input to the first neural network is raw ECG data (e.g., raw ECG waveforms). In addition to the raw ECG data, inputs to the first neural network can include information about the monitor 102, instantaneous heart rate, beat waveform location information, patient information, and preceding deep neural network (DNN) feature spaces. The output of the first neural network is data that identifies each beat's classification and affinity to similar heartbeats (e.g., beats that have the most similar features).

In certain instances, the first neural network is an autoencoder DNN. Autoencoder DNNs can be designed to take a large set of input data and extract features into a much smaller latent space which can be reconstructed into an approximation of the original input data. The autoencoder DNN of the present disclosure is programmed to extract the determinative features of beats' waveforms that can be used to accurately decide which beats are similar. As one example, the autoencoder DNN can transform a waveform of a beat from 500 datapoints to 8 datapoints, and these fewer datapoints may be those that are most likely to be helpful in distinguishing between different types of beats (e.g., supraventricular, ventricular, normal).

The autoencoder DNN of the present disclosure can be trained and structured to have an imbalanced encoder and decoder—where the encoder is a deep DNN while the decoder is a simpler neural network. During the training process, the first neural network is trained to match the output data to the input as closely as possible. Because of the imbalanced approach, the encoder is forced to do most of the learning thus creating a more complete latent space. The resulting latent space is then passed through a clustering algorithm, which identifies the beats that have the most similar features and places similar beats into the same cluster group.

Figure 3A:
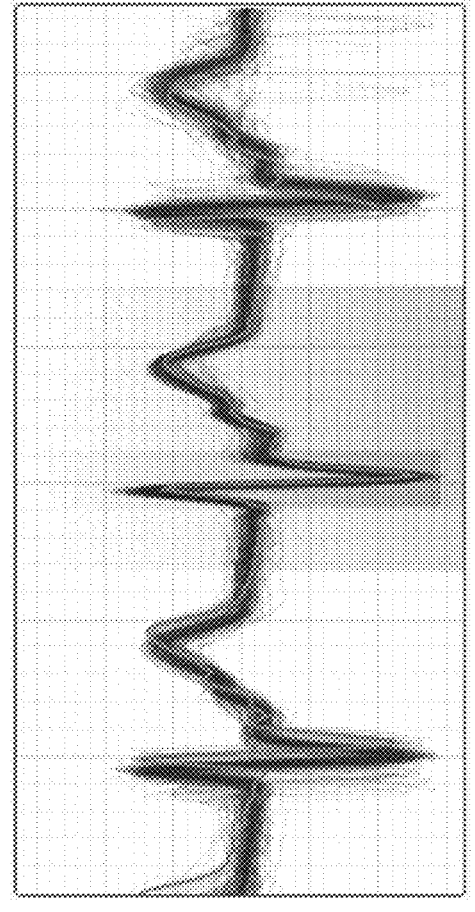
FIGS. 3A and 3B show views of beats grouped together, in accordance with certain instances of the present disclosure.
Figure 3B:
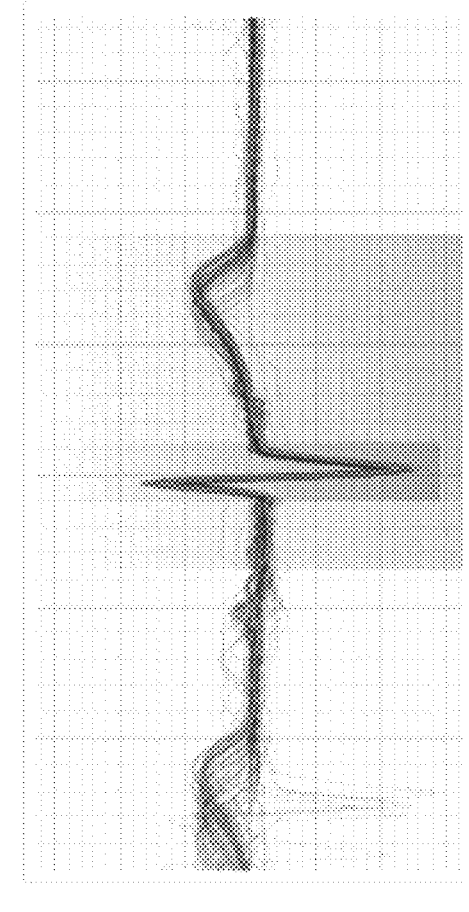

FIGS. 3A and 3B show examples of sets of beats that have been clustered together. Both Figures show multiple sets of short strips of ECG waveforms that are superimposed on each other. Each cluster can include hundreds or thousands of beats that have been grouped together by the autoencoder DNN. As can be seen, the beats in FIG. 3A all have a very similar profile to each other, and the beats in FIG. 3B have a very similar profile to each other. Each beat is aligned to have its QRS peak centered on the graph.

As described in more detail below, the cluster groups are ultimately presented to an end user in an ECG analysis tool and used for efficient review of a large amount of ECG data (e.g., one or more days of ECG data).

The second and third neural networks can include the neural networks described in U.S. patent application Ser. No. 16/695,534, which is hereby incorporated by reference in its entirety. The second neural network can be a deep convolutional neural network and the third neural network can be a deep fully-connected neural network. The deep convolutional neural network receives one or more sets of beats (e.g., beat trains with 3-10 beats) which are processed through a series of layers in the deep convolutional neural network. The series of layers can include a convolution layer to perform convolution on time series data in the beat trains, a batch normalization layer to normalize the output from the convolution layer (e.g., centering the results around an origin), and a non-linear activation function layer to receive the normalized values from the batch normalization layer. The beat trains then pass through a repeating set of layers such as another convolution layer, a batch normalization layer, a non-linear activation function layer. This set of layers can be repeated multiple times.

The deep fully connected neural network receives RR-interval data (e.g., time intervals between adjacent beats) and processes the RR-interval data through a series of layers: a fully connected layer, a non-linear activation function layer, another fully connected layer, another non-linear activation function layer, and a regularization layer. The output from the two paths is then provided to the fully connected layer. The resulting values are passed through a fully connected layer and a softmax layer to produce probability distributions for the classes of beats.

If the machine learning model 108 determines that the ECG data most closely resembles a labeled ECG data associated with a cardiac event, then the machine learning model 108 may determine that the patient 10 has experienced that cardiac event. Additionally, the machine learning model 108 may measure or determine certain characteristics of the cardiac activity of the patient 10 based on the ECG data. For example, the machine learning model 108 may determine a heart rate, a duration, or a beat count of the patient 10 during the cardiac event based on the ECG data. The server 106 stores the cardiac event (and associated metadata such as information like beat classification, heart rate, duration, beat count, etc.) in a database for storage. Subsequently, the server 106 may retrieve the cardiac event and associated information from the database.

In certain instances, the mobile device 104 (or monitor 102) may initially classify a cardiac event based on the ECG data. The server 106 may then re-classify or confirm the cardiac event using the machine learning model 108. Doing so allows for a more computationally-expensive analysis of the ECG data to be performed using the computing resources of the server 106, rather than the limited resources of the mobile device 104.

In certain instances, once the ECG data is processed by the machine learning model 108, the ECG data is made available for the report platform 112. As will be described in more detail below, the report platform 112 can be accessed by a remote computer 116 (e.g., client device such as a laptop, mobile phone, desktop computer, and the like) by a user at a clinic or lab 118.

In other instances, the cardiac event router 110 is used to determine what platform further processes the ECG data based on the classification associated with the cardiac event. For example, if the identified cardiac event is critical or severe, the cardiac event router 110 can flag or send the ECG data, etc., to the notification platform 114. The notification platform 114 can be programmed to send notifications (along with relevant ECG data and associated metadata) immediately to the patient's physician/care group remote computer 116 and/or to the patient 10 (e.g., to their computer system, e-mail, mobile phone application).

Report Platform

Figure 2:
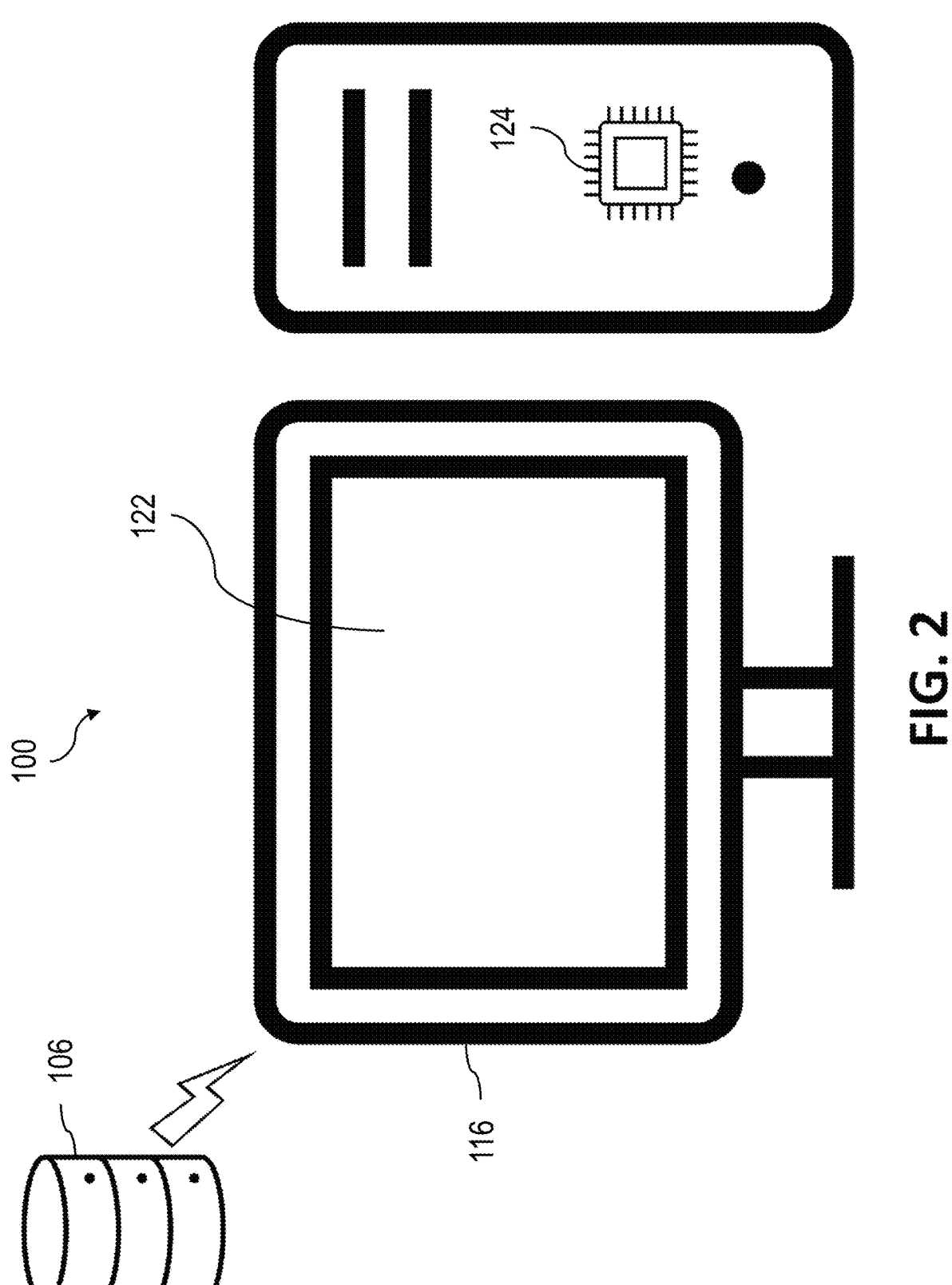
FIG. 2 shows a server, remote computer, and user interface, in accordance with certain instances of the present disclosure.

FIG. 2 shows the server 106 communicatively coupled (e.g., via a network) to the remote computer 116. In the example of FIG. 2, the remote computer 116 includes a monitor showing a user interface 122 (hereinafter "the UI 122" for brevity) that displays features of the report platform 112 hosted by the server 106. The UI 122 includes multiple pages or screens for tracking and facilitating analysis of patient ECG data.

In certain instances, the report platform 112 is a software-as-a-service (SaaS) platform hosted by the server 106. To access the report platform 112, a user (e.g., a technician) interacts with the UI 122 to log into the report platform 112 via a web browser such that the user can use and interact with the report platform 112. When the user at the clinic or lab 118 is ready to analyze ECG data of a patient, the user can select a patient's profile through the UI 122.

The server 106 (e.g., via programming associated with the report platform 112) can start a process for sending data to the remote computer 116. This data includes the ECG data and metadata associated with the ECG data. As noted above, once the ECG data from the monitored patients has been collected, the machine learning model 108 may determine certain characteristics of the cardiac activity of the patient 10 based on the ECG data, including estimating that a cardiac event has occurred and associating or generating metadata for the determined events. The metadata can include information about the patient 10, a heart rate of the patient 10 during the cardiac event, a duration of the cardiac event, a beat count of the cardiac event, a confidence level of the machine learning model's identification of the cardiac event, and/or a beat classification (e.g., normal, ventricular, supraventricular, unclassified).

In certain instances, the machine learning model 108 assigns each beat with a beat classification and also assigns, for certain groups and patterns of beats, a cardiac event type (e.g., atrial fibrillation, ventricular tachycardia, flutter). To distinguish among the beats, each individual beat can therefore be assigned a unique identifier (e.g., a unique number).

Accessing, processing, and displaying one or more days' worth of ECG data and metadata can consume a large amount of computing resources, network bandwidth resources, and human resources. To help alleviate burdens on these resources, the server 106 (e.g., via the report platform 112) can selectively transmit packages of ECG data and metadata to the remote computer 116.

The initial packages of data can include: (1) short strips (e.g., 60-second strips) of ECG data surrounding detected cardiac events, (2) metadata associated with the strips, and (3) executable code (e.g., JavaScript code). In certain instances, only the ECG data associated with highest priority cardiac events are initially transferred. After the initial packages of data are transmitted from the server to the remote computer 116, additional packages of data can be transmitted in response to selections made by the user in the U 1122.

Report Build Page

With these initial packages of data, the user has access (via the remote computer 116 and the UI 122) to a report build page 200 shown in FIGS. 4-12B. The report build page 200 facilitates analysis of cardiac events and metadata associated with the cardiac events. The pages are generated at the remote computer 116 based on the packages of data and they are selectively displayed via the UI 122. As will be described in more detail below, as the user interacts with the report build page 200, the metadata is updated in real time at the remote computer 116.

Figure 4:
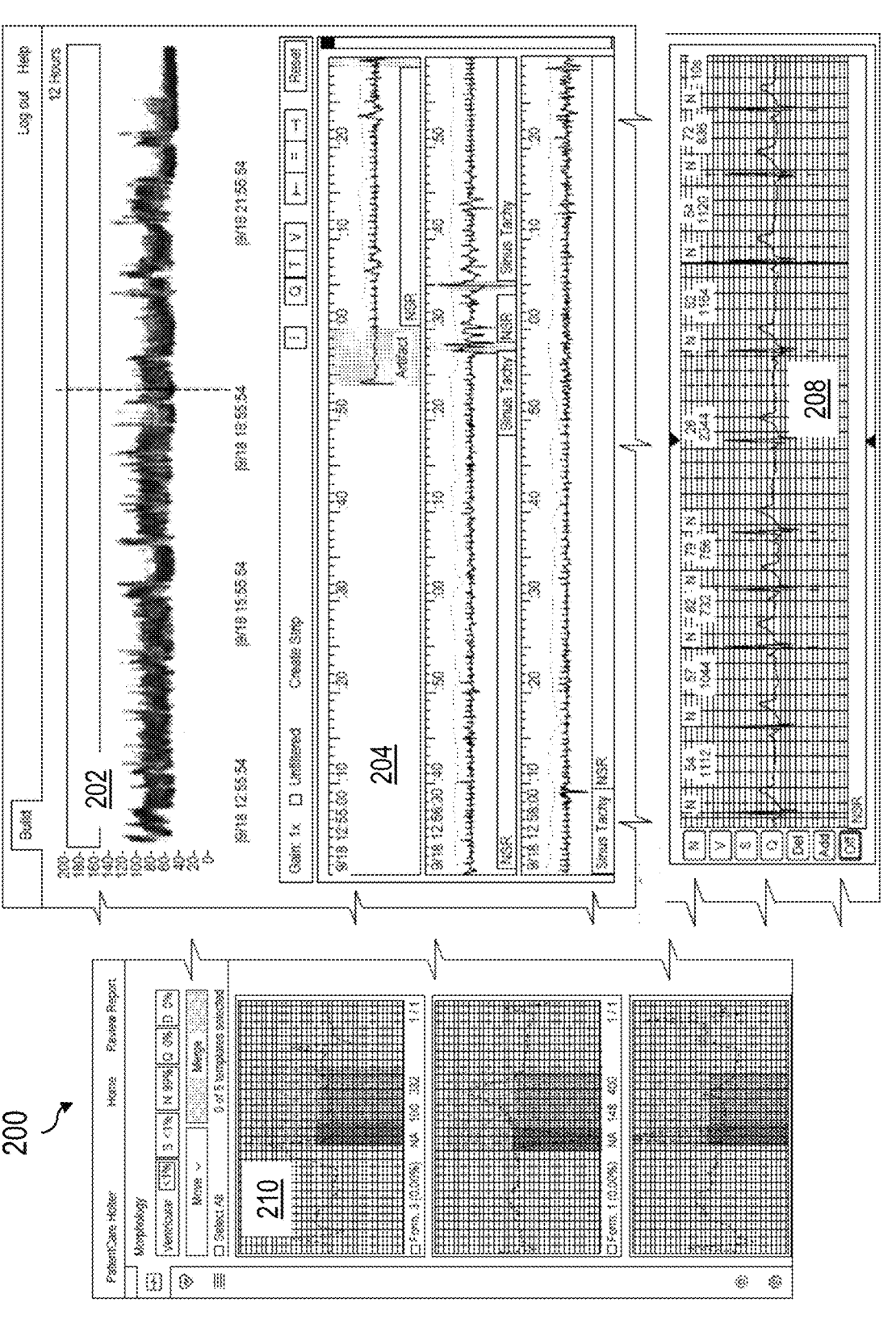
FIGS. 4-12B show various views of a report building user interface, in accordance with certain instances of the present disclosure.

FIG. 4 shows a screenshot of the report build page 200. The report build page 200 is used by a user to review and analyze a patient's ECG data and metadata. The report build page 200 includes multiple windows for displaying data, plots, icons, links, markers, indicators, and the like.

Window 202 displays a heart rate plot of multiple days' worth of ECG data. This window 202 provides an initial visual insight into which periods of time appear to contain abnormal heart rate activity. In the example of FIG. 3, the window 202 displays four days of ECG data, although shorter or longer time periods could be displayed by default or changed by the user.

Window 204 allows the user to view a shorter plot of ECG data. For example, the window 204 may display ECG data associated with a detected cardiac event along with ECG data preceding and following the detected event. This window 204 provides visual insight into the onset of a detected event and whether the detected event is perhaps an artifact, follow-on event, etc. As the user scrolls through the window 204, the window 202 can display an indicator (e.g., a vertical line) showing the location of the ECG data of window 204 within the heart rate plot of window 202.

Window 208 shows a plot of ECG data (e.g., approximately 10 beats) that is shorter than the plots of windows 202 and 204. Window 208 displays a closer-up view of a portion of the ECG data of windows 202 and 204. The user can use window 204 to select which shorter set of ECG data is displayed in the window 208. Each of the windows 202, 204, and 208 can include markers, indicators, icons, etc., to visually note the location of detected cardiac events within the strips of ECG data.

Beat Morphology

To the left of the report build page 200 is a beat morphology window 210 (hereinafter "the morphology window 210"), which includes multiple individual sub-windows that display plots of one or more individual beats. The user can use the morphology window 210 to select beats, which can result in updating the windows 202, 204, and 208. For example, the windows 202, 204, and 208 can be updated to show ECG data surrounding the beat selected in the morphology window 210.

Figures 5, 6:
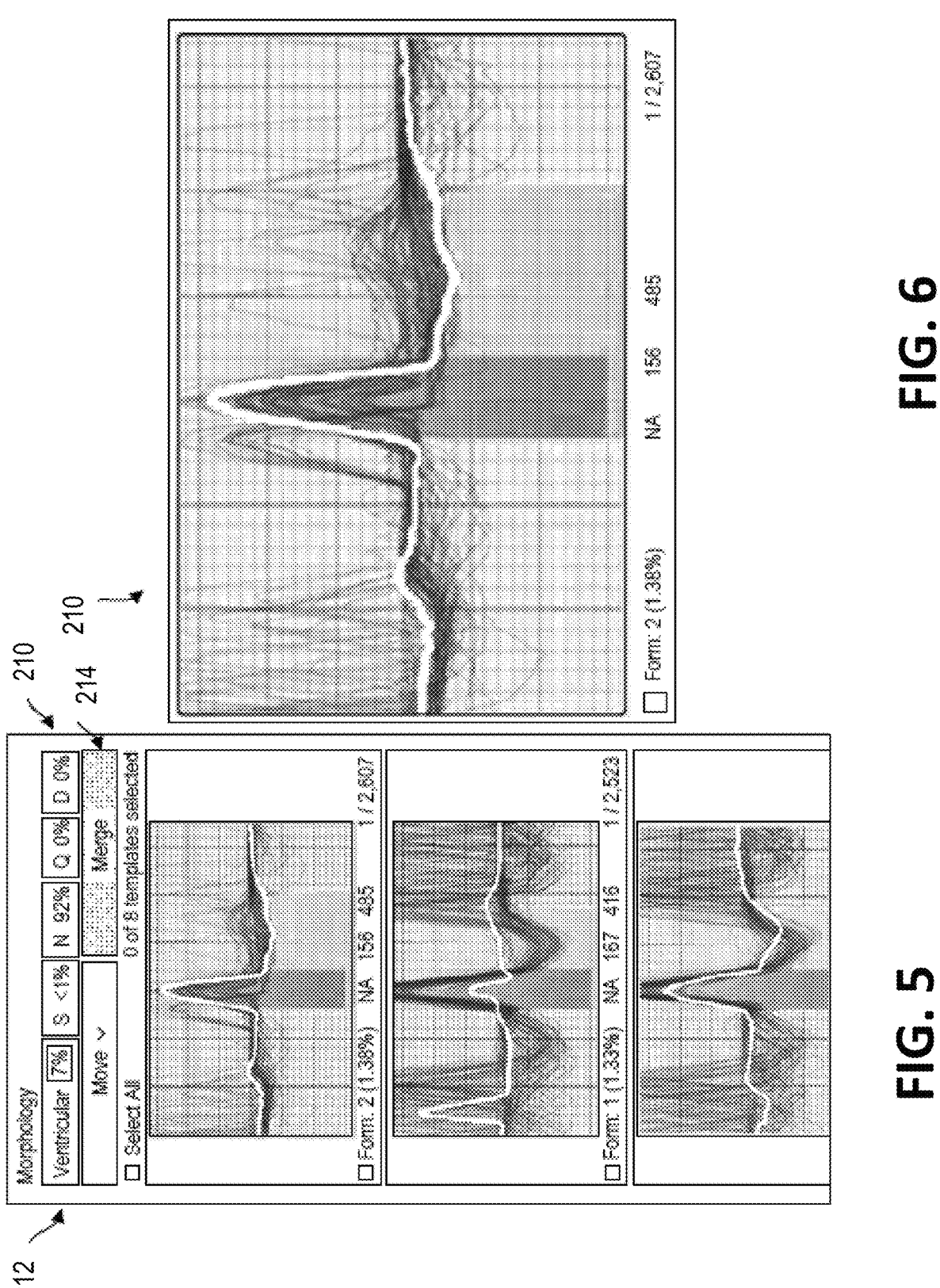

FIGS. 5 and 6 show closer-up views of the morphology window 210. FIG. 5 shows the morphology window 210 as displaying multiple sub-windows. Each sub-window can display multiple plots of beats that have been characterized (e.g., by the machine learning model 108) with the same type of cardiac event. The user can select the type of cardiac event (e.g., atrial fibrillation, ventricular tachycardia) from a menu button 212 to display beats associated with the selected cardiac event in the sub-window.

The user can then select individual or sets of beat plots in the sub-window (or all beats associated with the sub-window) and, if desired, change the beat classification (e.g., from an "S" beat to a "V" beat or an "N" beat). Additionally, instead of selecting individual beats, the user can select all beats associated with a given cardiac event and change the beat classification to a different beat classification. Because the machine learning model 108 assigns each beat with an initial beat classification, the report build page 200 can be used to make mass updates to the metadata associated with similarly characterized beats. For example, in FIG. 6, the cardiac event type associated with the sub-window is shown as being associated with 2,607 beats. Using the morphology window 210 of the report build page 200, the user can recharacterize each of those 2,607 beats in one operation (e.g., change the initial classification of the 2,607 beats to a subsequent beat classification). The user can also merge sub-windows using a merge button 214 such that the beats in the two or more sub-windows are characterized with the same cardiac event type.

Figures 7, 8:
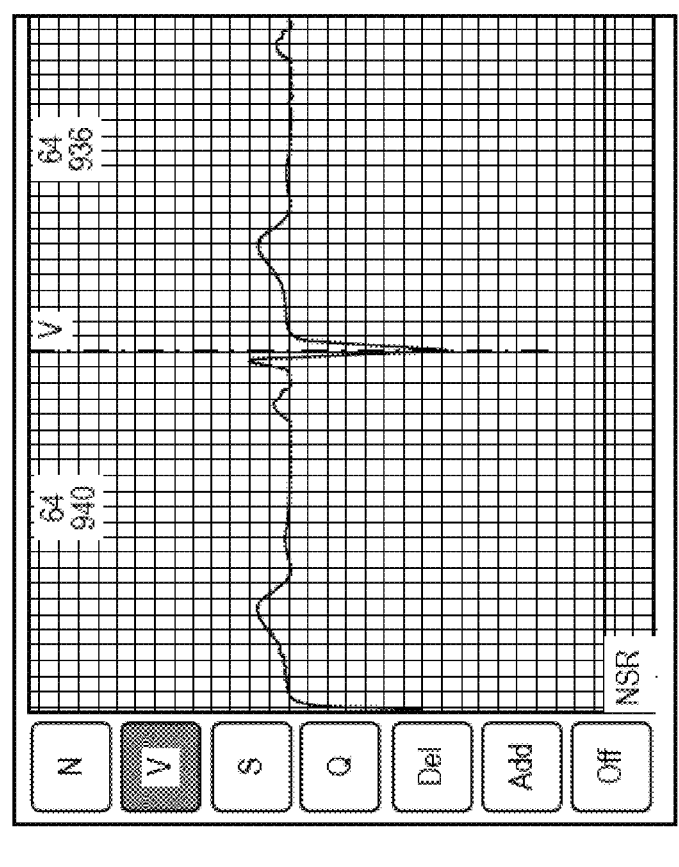

FIGS. 7 and 8 show other views of how a user can utilize a UI to make changes to beats. In FIG. 7, the user can select a window showing a grouping of similarly classified beats and then select a dropdown menu of options for reclassifying the selected grouping of beats. As shown in FIG. 7, potential options for classification include normal beats, ventricular beats, supraventricular beats, and unclassified beats. FIG. 8 shows another view where a user can select a beat or set of beats and use buttons to change the classification associated with the selected beat(s).

Using one or more of the approaches described above, metadata for thousands to hundreds of thousands (or millions, for long studies) of beats can be updated en masse through the UI. Because a set of ECG data may represent tens of thousands, hundreds of thousands, or even millions of individual beats, this ability to make mass updates to beats saves the user time in analyzing ECG data and, ultimately, building a report.

Event Reclassification

As noted above, one input to determining the type of cardiac event includes the types or classifications of beats that occurred during the cardiac event. As such, when a user makes mass updates to beat classifications, the initial cardiac event classifications should be reassessed. Instances of the present disclosure describe approaches for reassessing cardiac event classifications when the underlying beat classifications are changed. Because reassessing the ECG data may occur at the remote computer 116 (which may not include a machine learning model or have the computational resources to quickly operate a machine learning model), the approaches described herein can be carried out without using the machine learning model 108 operated at the server 106 or another such machine learning model. For example, the approaches may be carried out on the remote computer 116 by executing code sent to the remote computer 116 by the server 106.

In certain instances, in response to beat reclassifications, the remote computer 116 applies a state machine to determine whether and how the initial cardiac event classifications should be reclassified. Inputs to the state machine include the updated (or subsequent) beat classifications, beat classifications surrounding each detected cardiac event, and the initial rhythm classifications of the detected cardiac events surrounding a given cardiac event. In certain instances, the state machine is only applied to regions of the ECG data (or detected cardiac events) that involve one or more reclassified beats. The state machine outputs an annotation indicating a proposed rhythm classification for an underlying range of beats.

A multi-step algorithm is applied on the output of the state machine to apply the proposed rhythm classification changes to the existing rhythm classifications. The multi-step algorithm considers nearby rhythm classifications as well as heart rate and regularity in the affected regions. In addition to reclassifying cardiac events, in certain instances, the output of the state machine and multi-step algorithm results in adjacent sets of rhythms being merged into a single cardiac event and rhythm classification.

The approaches described above allow a user to make mass changes to ECG data by focusing attention on beat reclassifications. FIGS. 9A-12B provide examples of how changes to beat classifications can affect rhythm classifications.

In each of these pairs of Figures, the top figure shows a strip of ECG data containing a cardiac event with its initial rhythm (or event) classification—if any—and beat classifications, and the bottom figure shows the strip of ECG data with modified (or subsequent) rhythm (or event) and beat classifications. The beat classifications are shown in icons at the top of the strip of ECG data. Beats classified as being normal beats are indicated by the letter "N" in the icons, ventricular beats are denoted with a "V", and supraventricular beats are denoted with an "S". The rhythm classifications of the cardiac event are shown in ribbons or bands that extend horizontally at the bottom of the strip of ECG data. The length of the ribbons/band visually shows the length of the cardiac event. As noted above, the initial classifications are based on the metadata generated by the machine learning model 108 at the server 106 and received by the remote computer 116. The strips of ECG data also displays the RR intervals (in terms of milliseconds) for respective pairs of beats.

Figure 9A:
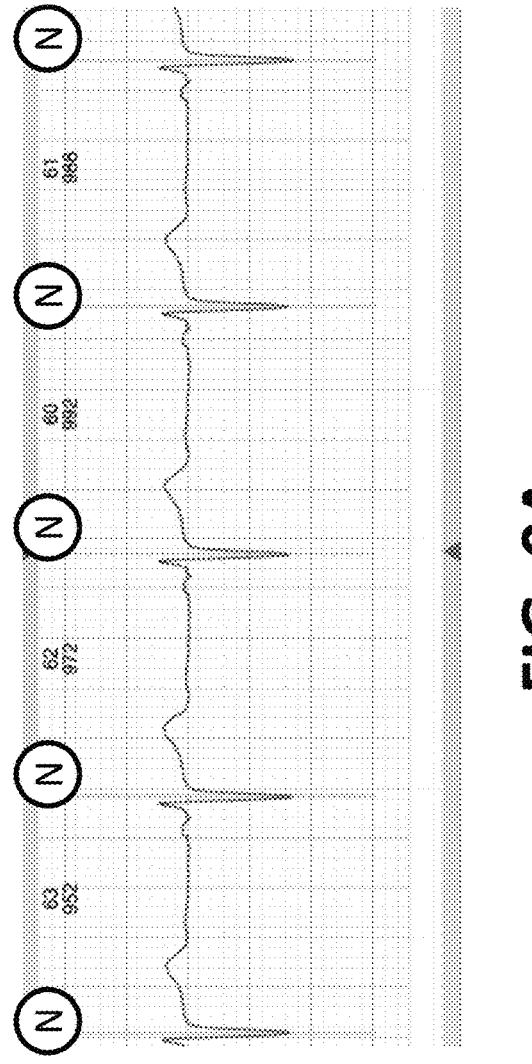
Figure 9B:
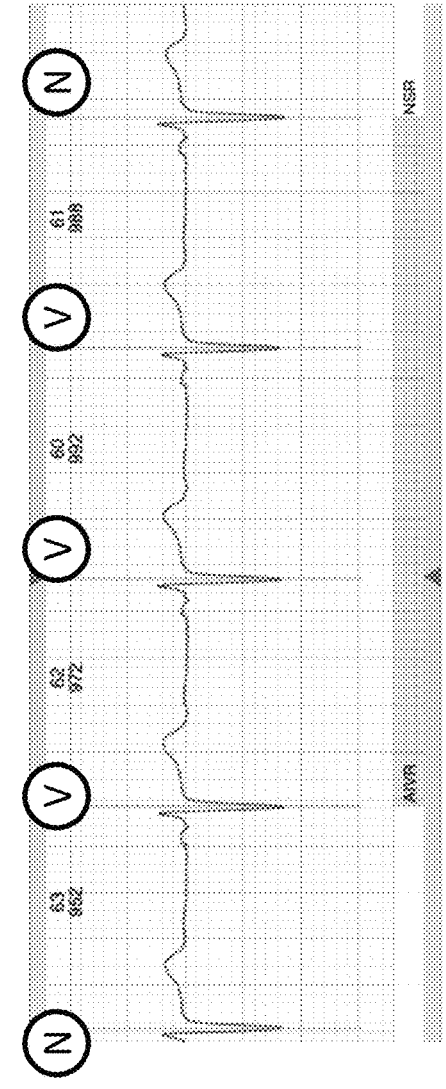

In the example of FIGS. 9A and 9B, the beat classification for three beats was changed from normal (N) to ventricular (V) in the context of an existing normal sinus rhythm (NSR) classification. Ventricular rhythms will be created where three or more consecutive ventricular (V) beats occur. In the example of FIGS. 9A and 9B, the regularity of the beats qualified the rhythm as either an idioventricular rhythm (IVR) or accelerated idioventricular rhythm (AIVR), and then the average heart rate of the three beats was used to select the label of AIVR. Finally, surrounding rhythm classifications were updated too, including the onset/offset of a surrounding NSR label.

Figures 10A, 10B:
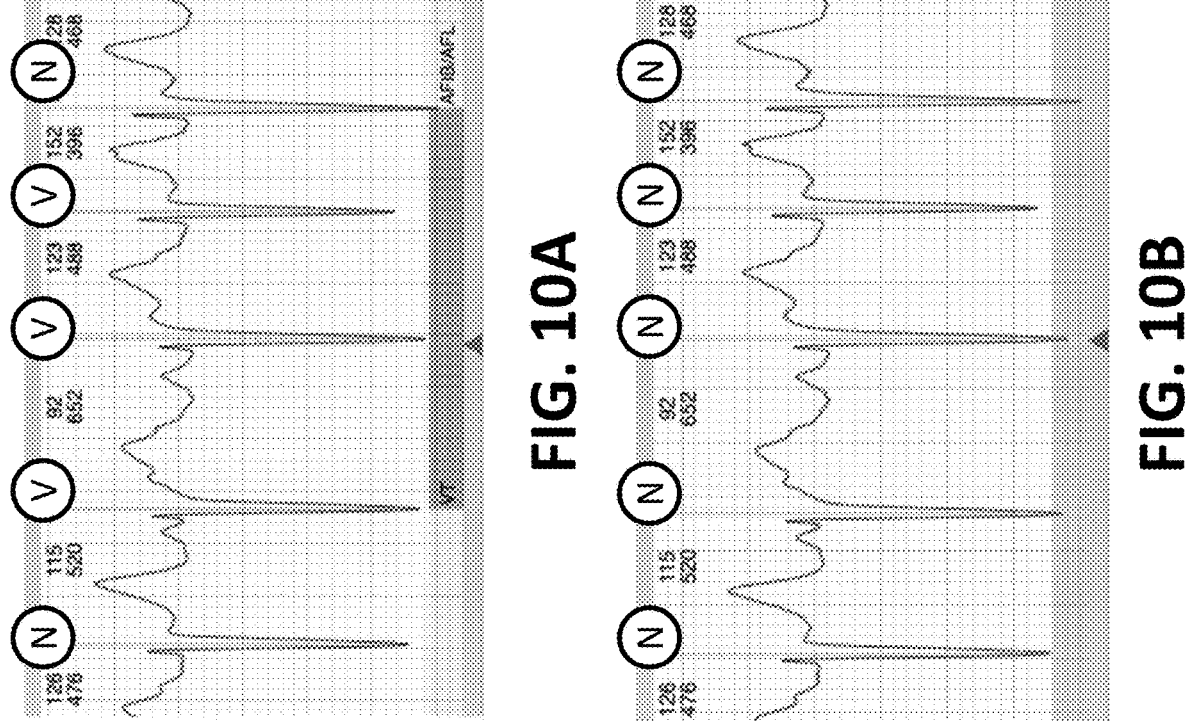

In the Example of FIGS. 10A and 10B, the beat classification for three beats was changed from ventricular (V) to normal (N) in the context of atrial fibrillation (AFIB). Typically, a sinus rhythm classification will be created when three or more consecutive normal (N) beats occur. In this case, however, an AFIB rhythm label was created due to the existing AFIBs on both sides. Finally, surrounding rhythm classifications were updated too, including the merging/joining of the affected regions into a single contiguous AFIB cardiac event.

Figure 11A:
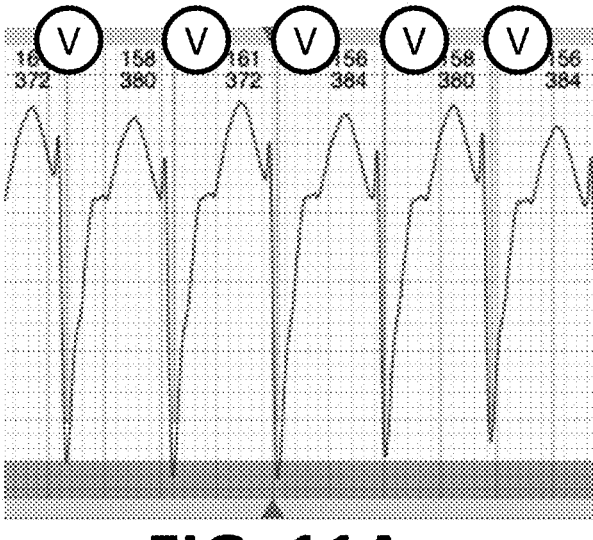
Figure 11B:
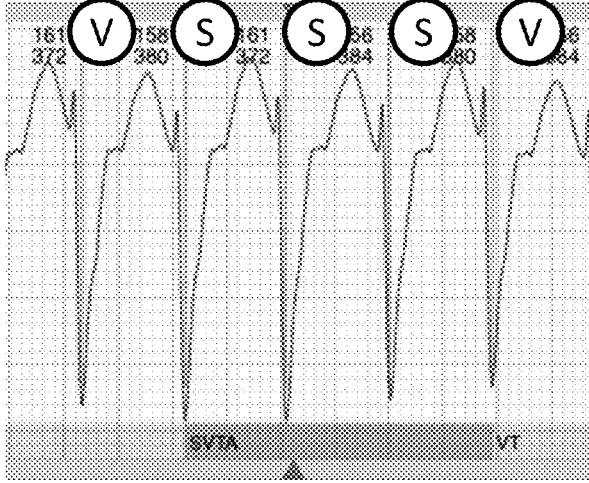

In the Example of FIGS. 11A and 11B, the beat classification for three beats was changed from ventricular (V) to supraventricular (S) in the context of ventricular tachycardia (VT). A supraventricular rhythm classification will be created when three or more consecutive supraventricular (S) beats occur. In this case, a supraventricular tachycardia (SVTA) label was selected based on heart rate of the beats. Finally, surrounding rhythm classifications were updated too, including the onset/offset of the surrounding VT labels.

Figure 12A:
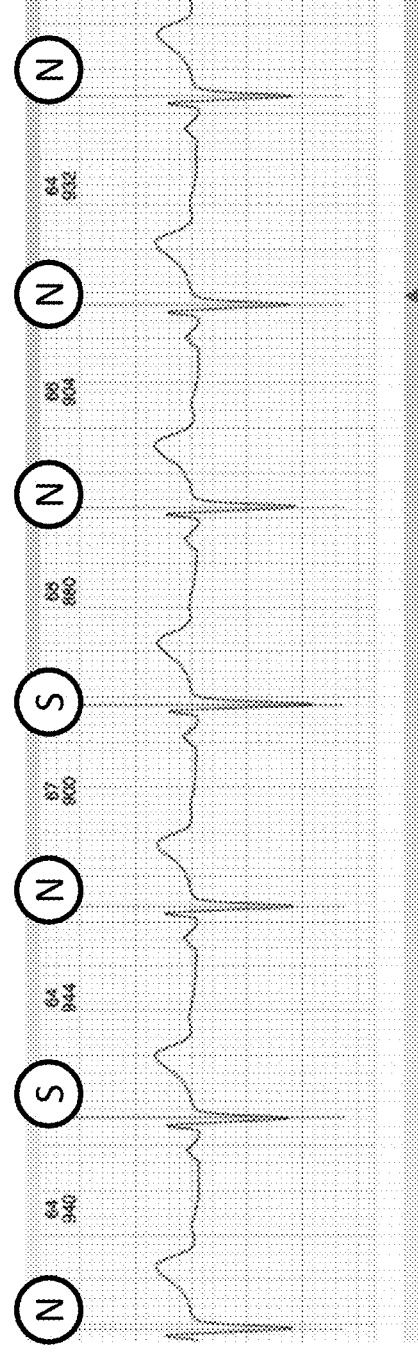
Figure 12B:
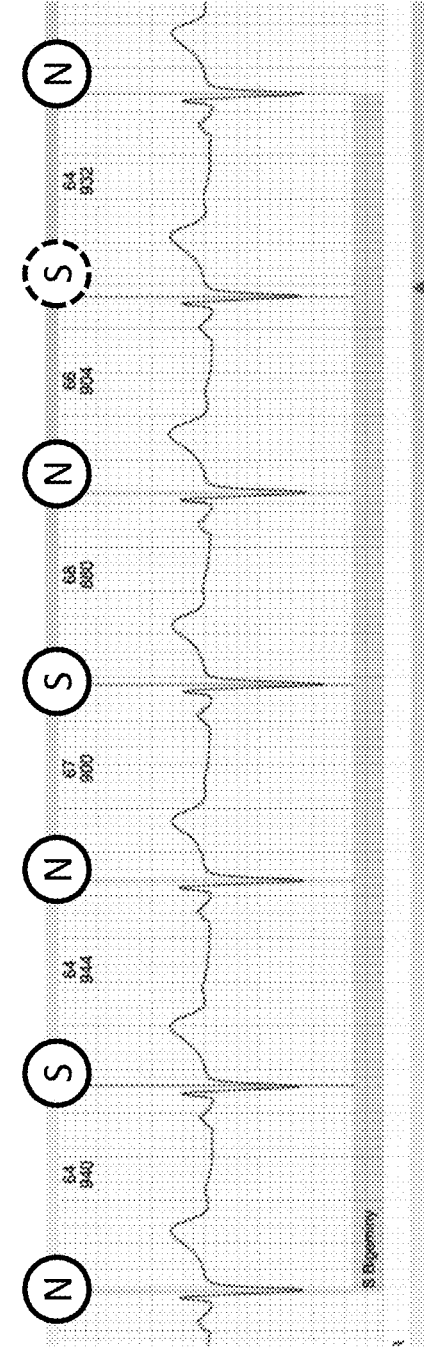

In the Example of FIGS. 12A and 12B, the beat classification for one beat from was changed from normal (N) to supraventricular (S) in the context of normal sinus rhythm (NSR). A supraventricular bigeminy/trigeminy classification will be created when the applicable beat pattern occurs. In this case, a supraventricular bigeminy label was selected based on the beat pattern.

To save processing and network resources and to allow these changes to metadata to occur in real-time, the calculations and changes to the cardiac event classifications and the automatic updates to the beat classifications can be carried out locally on the remote computer 116—as opposed to sending data back and forth between the server 106 and the remote computer 116. For example, the reclassifications can be carried out using cache memory 124 (shown in FIG. 1) and processing capabilities (e.g., one or more micropro-cessors) of the remote computer 116. To enable local pro-cessing and updating, the report platform 112 can send the remote computer 116 code to execute locally. This code uses (or operates on) the outputs of the machine learning model 108 such as the beat classifications and rhythm classifica-tions (as opposed to the underlying or raw ECG data), which reduces the computational resources needed to process the changes made by user locally at the remote computer 116. In certain embodiments, this code is executed by an internet browser operating on the remote computer 116.

In certain instances, once a final report is built and complete, the remote computer 116 can send any changes to the metadata (e.g., the subsequent beat classifications and the subsequent rhythm classifications) to the server 106 and its database. The server 106 can then replace the metadata initially created by the machine learning model (and saved to the database) with the metadata generated by the remote computer while the user was reviewing and editing the metadata. As such, if the ECG and metadata need to be accessed again, the server's database has the most recent version of the metadata. Further, the machine learning model 108 may be further trained on the metadata generated by the user at the remote computer.

Computing Devices and Systems

Figure 13:
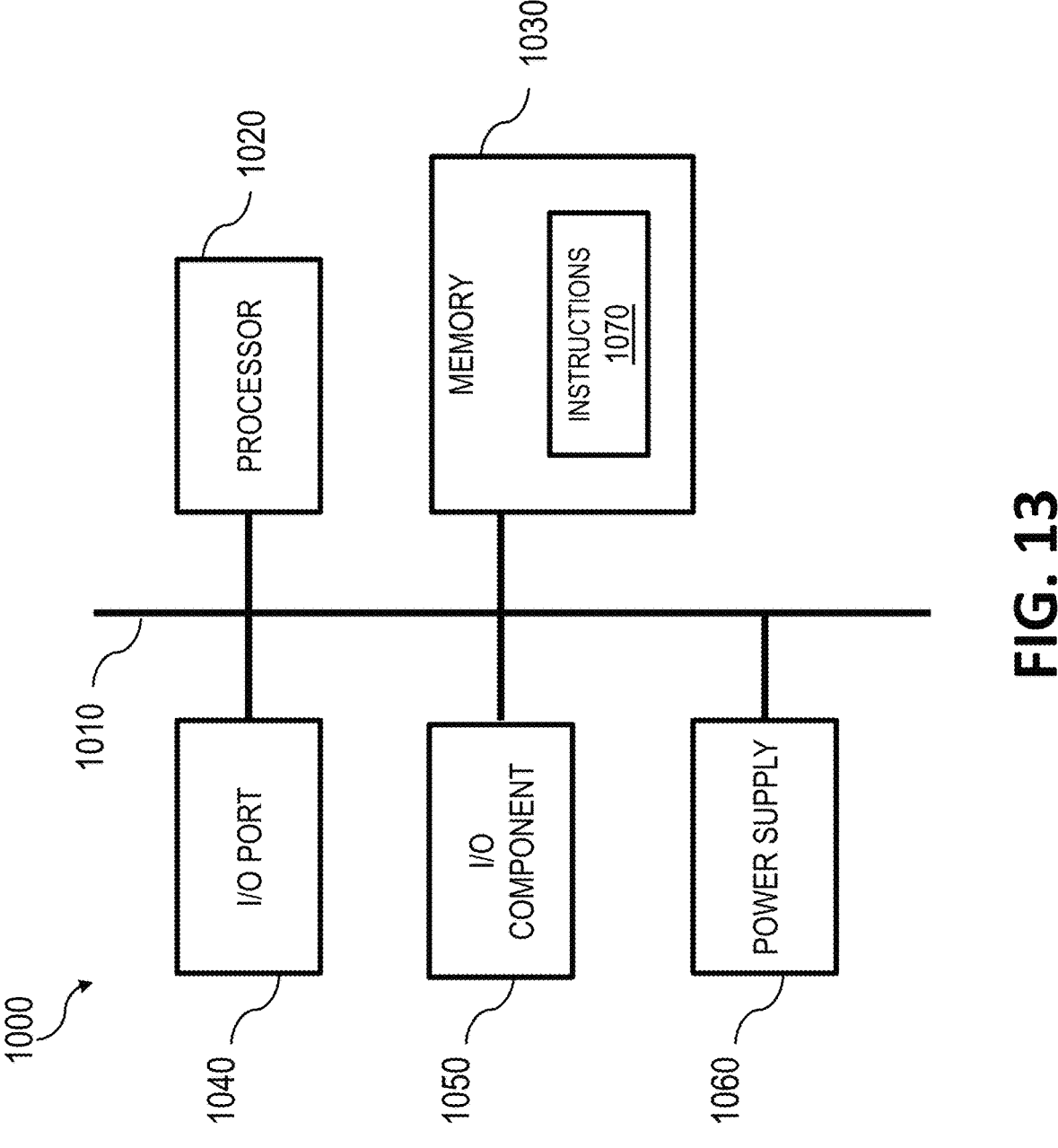
FIG. 13 is a block diagram depicting an illustrative computing device, in accordance with instances of the disclosure.

FIG. 13 is a block diagram depicting an illustrative computing device 1000, in accordance with instances of the disclosure. The computing device 1000 may include any type of computing device suitable for implementing aspects of instances of the disclosed subject matter. Examples of computing devices include specialized computing devices or general-purpose computing devices such as workstations, servers, laptops, desktops, tablet computers, hand-held devices, smartphones, general-purpose graphics processing units (GPGPUs), and the like. Each of the various compo-nents shown and described in the Figures can contain their own dedicated set of computing device components shown in FIG. 13 and described below. For example, the mobile device 104, the server 106, and the remote computer 116 can each include their own set of components shown in FIG. 13 and described below.

In instances, the computing device 1000 includes a bus 1010 that, directly and/or indirectly, couples one or more of the following devices: a processor 1020, a memory 1030, an input/output (I/O) port 1040, an I/O component 1050, and a power supply 1060. Any number of additional components, different components, and/or combinations of components may also be included in the computing device 1000.

The bus 1010 represents what may be one or more busses (such as, for example, an address bus, data bus, or combi-nation thereof). Similarly, in instances, the computing device 1000 may include a number of processors 1020, a number of memory components 1030, a number of I/O ports 1040, a number of I/O components 1050, and/or a number of power supplies 1060. Additionally, any number of these components, or combinations thereof, may be distributed and/or duplicated across a number of computing devices.

In instances, the memory 1030 includes computer-read-able media in the form of volatile and/or nonvolatile memory and may be removable, nonremovable, or a com-bination thereof. Media examples include random access memory (RAM); read only memory (ROM); electronically erasable programmable read only memory (EEPROM); flash memory; optical or holographic media; magnetic cas-settes, magnetic tape, magnetic disk storage or other mag-netic storage devices; data transmissions; and/or any other medium that can be used to store information and can be accessed by a computing device. In instances, the memory 1030 stores computer-executable instructions 1070 for caus-ing the processor 1020 to implement aspects of instances of components discussed herein and/or to perform aspects of instances of methods and procedures discussed herein. The memory 1030 can comprise a non-transitory computer read-able medium storing the computer-executable instructions 1070.

The computer-executable instructions 1070 may include, for example, computer code, machine-useable instructions, and the like such as, for example, program components capable of being executed by one or more processors 1020 (e.g., microprocessors) associated with the computing device 1000. Program components may be programmed using any number of different programming environments, including various languages, development kits, frameworks, and/or the like. Some or all of the functionality contemplated herein may also, or alternatively, be implemented in hardware and/or firmware.

According to instances, for example, the instructions 1070 may be configured to be executed by the processor 1020 and, upon execution, to cause the processor 1020 to perform certain processes. In certain instances, the processor 1020, memory 1030, and instructions 1070 are part of a controller such as an application specific integrated circuit (ASIC), field-programmable gate array (FPGA), and/or the like. Such devices can be used to carry out the functions and steps described herein.

The I/O component 1050 may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The devices and systems described herein can be communicatively coupled via a network, which may include a local area network (LAN), a wide area network (WAN), a cellular data network, via the internet using an internet service provider, and the like.

Aspects of the present disclosure are described with reference to flowchart illustrations and/or block diagrams of methods, devices, systems and computer program products. It will be understood that each block of the flowchart illustrations and/or block diagrams, and combinations of blocks in the flowchart illustrations and/or block diagrams, can be implemented by computer program instructions.

Various modifications and additions can be made to the exemplary instances discussed without departing from the scope of the disclosed subject matter. For example, while the instances described above refer to particular features, the scope of this disclosure also includes instances having different combinations of features and instances that do not include all of the described features. Accordingly, the scope of the disclosed subject matter is intended to embrace all such alternatives, modifications, and variations as fall within the scope of the claims, together with all equivalents thereof.

We claim:

1. A system comprising:
a remote computing system comprising: a user interface (UI), a first processor, and a first computer-readable medium having a first set of computer-executable instructions embodied thereon, the first set of instructions configured to be executed to cause the system to:
after receiving electrocardiogram (ECG) data and metadata including an initial cardiac event classification and an initial beat classification for beats occurring during a first event associated with the initial cardiac event classification: display the ECG data in the UI;
receive, via a user selection in the UI, a command to change the initial beat classifications to subsequent beat classifications; and
automatically modify the initial cardiac event classification to a subsequent cardiac event classification based on the subsequent beat classifications selected via the UI.

2. The system of claim 1, wherein the automatically modifying the initial cardiac event classification to the subsequent cardiac event classification includes using a state machine.

3. The system of claim 2, wherein the state machine uses the subsequent beat classifications to determine the subsequent cardiac event classification.

4. The system of claim 2, wherein the state machine uses the initial beat classifications of beats surrounding the first event to determine the subsequent cardiac event classification.

5. The system of claim 2, wherein a multi-step algorithm receives outputs of the state machine, wherein the multi-step algorithm determines the subsequent cardiac event classification.

6. The system of claim 1, wherein the command causes the initial beat classifications to change to the subsequent beat classifications for thousands of individual beats.

7. The system of claim 1, wherein the metadata comprises initial cardiac event classifications and initial beat classification for beats occurring during multiple events, wherein only the initial cardiac event classifications associated with subsequent beat classifications are modified.

8. The system of claim 1, wherein the automatically modifying the initial cardiac event classification to the subsequent cardiac event classification causes initial separate events to merge into a single event.

9. The system of claim 1, wherein the first set of instructions further cause the first processor to:
display, via the UI in a single window, multiple superimposed plots of beats associated with the same initial beat classification.

10. The system of claim 9, wherein the command comprises selecting some or all of the beats in the single window and modifying the initial beat classifications to the subsequent beat classifications.

11. The system of claim 1, wherein the initial beat classifications are ventricular beats and the subsequent beat classifications are normal beats, wherein the initial cardiac event classification is a sinus rhythm and the subsequent event classification is an atrial fibrillation rhythm.

12. The system of claim 1, wherein the initial beat classifications are ventricular beats and the subsequent beat classifications are supraventricular beats, wherein the subsequent event classification is a supraventricular tachycardia event.

13. The system of claim 1, wherein the first set of instructions are configured to be executed via a web browser at the remote computing system.

14. The system of claim 1, further comprising:
a server comprising: a database, a second processor, and a second computer-readable medium having a second set of computer-executable instructions embodied thereon, the second set of instructions configured to be executed by the second processor to cause the second processor to:
determine, using a machine learning model operated by the server and based on ECG data, the initial cardiac event classification and the initial beat classifications;
store the initial cardiac event classification and initial beat classifications in the database;
transmit, to the remote computing system, strips of the initial ECG data, the initial cardiac event classification, the initial beat classifications, and the first set of instructions;
receive, from the remote computing system, the subsequent cardiac event classification and the subsequent beat classifications; and
replace, in the database, the initial cardiac event classification with the subsequent cardiac event classification and the initial beat classifications with the subsequent beat classifications.

15. A method comprising:

receiving, by a first computing system, electrocardiogram (ECG) data and metadata associated with the ECG data, the metadata comprising an initial cardiac event classification and an initial beat classification for each beat occurring during a first event associated with the initial cardiac event classification;

causing the ECG data to be displayed in a user interface (UI);

receiving a command, via the UI, to change the initial beat classifications to subsequent beat classifications; and automatically modifying, by the first computing system, the initial cardiac event classification to a subsequent cardiac event classification based on the subsequent beat classifications, wherein the automatically modifying comprises using a state machine, which uses the subsequent beat classifications to determine the subsequent cardiac event classification.

16. The method of claim 15, wherein the state machine uses the initial beat classifications of beats surrounding the first event to determine the subsequent cardiac event classification.

17. The method of claim 15, wherein the initial beat classifications are ventricular beats and the subsequent beat classifications are normal beats, wherein the initial cardiac event classification is a sinus rhythm and the subsequent event classification is an atrial fibrillation rhythm.

18. The method of claim 15, wherein the initial beat classifications are ventricular beats and the subsequent beat classifications are supraventricular beats, wherein the subsequent event classification is a supraventricular tachycardia event.

19. A system comprising:

a remote computing system comprising: a user interface (UI), a first processor, and a first computer-readable medium having a first set of computer-executable instructions embodied thereon, the first set of instructions configured to be executed to cause the system to:

after receiving electrocardiogram (ECG) data and metadata including an initial cardiac event classification and an initial beat classification for beats occurring during a first event associated with the initial cardiac event classification: display the ECG data in the UI;

receive, via a user selection in the UI, a single command to change the initial beat classifications to subsequent beat classifications for thousands of individual beats; and automatically modify the initial cardiac event classification to a subsequent cardiac event classification based on the subsequent beat classifications.

20. The system of claim 19, wherein the automatically modifying the initial cardiac event classification to the subsequent cardiac event classification includes using a state machine.

* * * * *